(12) United States Patent
Sterling

(10) Patent No.: US 9,816,895 B2
(45) Date of Patent: Nov. 14, 2017

(54) WIND TUNNEL FOR EROSION TESTING

(71) Applicant: The Boeing Company, Chicago, IL (US)

(72) Inventor: David E. Sterling, Seattle, WA (US)

(73) Assignee: The Boeing Company, Chicago, IL (US)

( * ) Notice: Subject to any disclaimer, the term of this patent is extended or adjusted under 35 U.S.C. 154(b) by 80 days.

(21) Appl. No.: 14/738,362

(22) Filed: Jun. 12, 2015

(65) Prior Publication Data

US 2016/0363505 A1 Dec. 15, 2016

(51) Int. Cl.
*G01M 9/04* (2006.01)
*G01N 17/00* (2006.01)

(52) U.S. Cl.
CPC ............ *G01M 9/04* (2013.01); *G01N 17/002* (2013.01)

(58) Field of Classification Search
CPC ............ G01M 9/04; G01M 9/00; G01M 9/02; G01M 9/06
USPC .......................................................... 73/147
See application file for complete search history.

(56) References Cited

U.S. PATENT DOCUMENTS

| | | | | |
|---|---|---|---|---|
| 4,474,140 A * | 10/1984 | Sternfeld | ............. | F01K 25/005 122/31.1 |
| 4,751,844 A * | 6/1988 | Matsushita | ............. | G01M 9/04 73/147 |
| 9,353,994 B1 * | 5/2016 | Allison, III | ............. | F24F 13/02 |
| 2010/0064793 A1 * | 3/2010 | Fritz | ..................... | G01M 9/067 73/147 |
| 2010/0132446 A1 * | 6/2010 | Corder | .................. | G01M 9/062 73/147 |
| 2013/0180325 A1 * | 7/2013 | Spandl | ................... | G01N 15/02 73/147 |
| 2014/0157872 A1 * | 6/2014 | Welland | ............. | G01N 15/0656 73/28.02 |
| 2015/0375125 A1 * | 12/2015 | Lurie | ..................... | A63G 31/00 472/49 |

* cited by examiner

*Primary Examiner* — Lisa Caputo
*Assistant Examiner* — Tarun Sinha
(74) *Attorney, Agent, or Firm* — Duft Bornsen & Fettig LLP

(57) ABSTRACT

Test systems for simulating an environment for erosion testing. An exemplary system includes a wind tunnel having a fan unit at one end and an exhaust unit at the other, and a test fixture that secures a specimen under test in a path of the air flow created in the wind tunnel. The system also includes a water injection unit installed between the fan unit and the test fixture that emits water droplets into the air flow. A controller of the system identifies a test profile indicating conditions for a test of the specimen, and varies the speed of the air flow, the orientation of the specimen, and/or a flow rate of water out of a nozzle of the water injection unit during the test to simulate the conditions indicated in the test profile.

19 Claims, 10 Drawing Sheets

FIG. 3

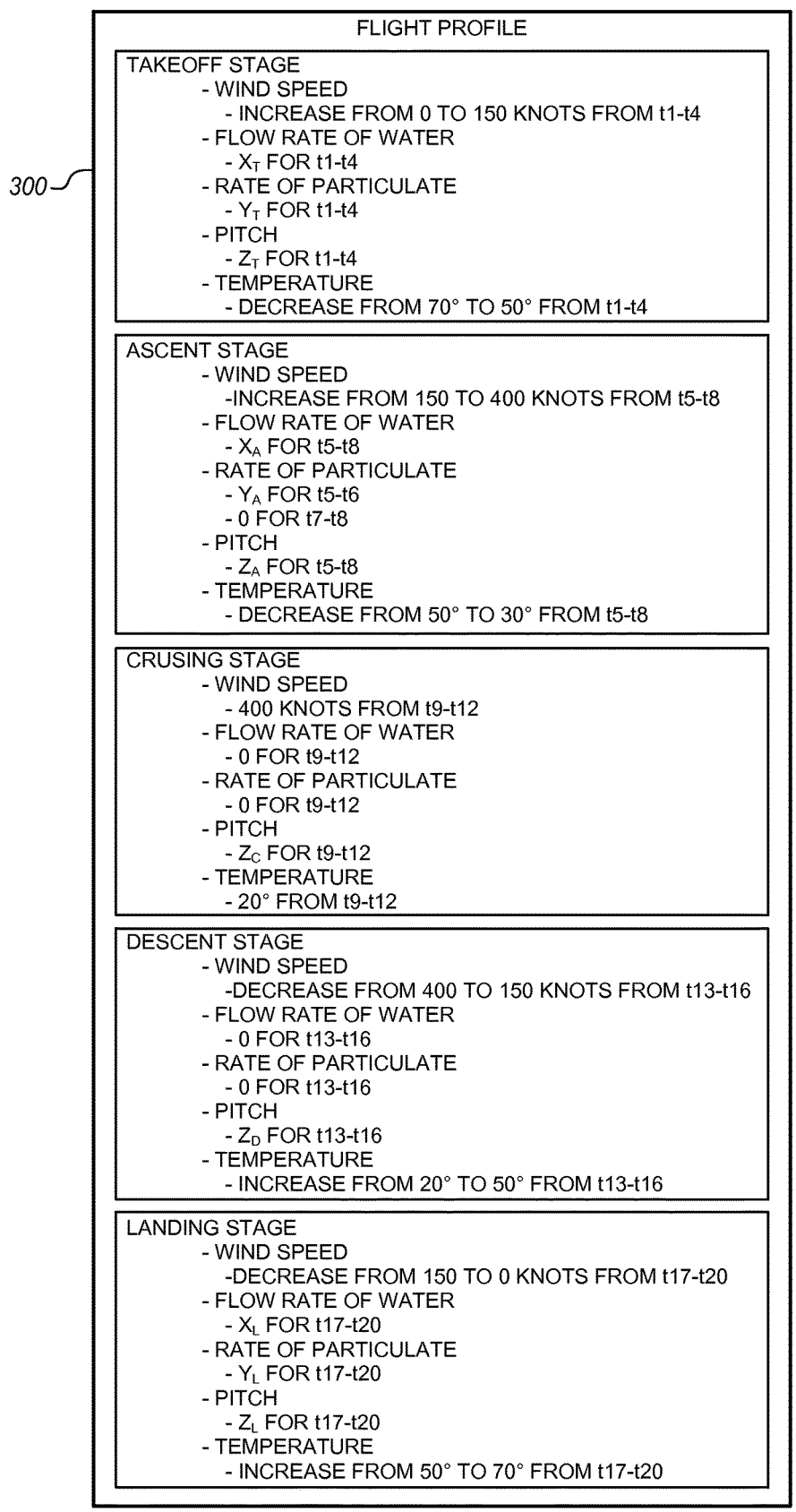

FLIGHT PROFILE

TAKEOFF STAGE
- WIND SPEED
  - INCREASE FROM 0 TO 150 KNOTS FROM t1-t4
- FLOW RATE OF WATER
  - $X_T$ FOR t1-t4
- RATE OF PARTICULATE
  - $Y_T$ FOR t1-t4
- PITCH
  - $Z_T$ FOR t1-t4
- TEMPERATURE
  - DECREASE FROM 70° TO 50° FROM t1-t4

ASCENT STAGE
- WIND SPEED
  - INCREASE FROM 150 TO 400 KNOTS FROM t5-t8
- FLOW RATE OF WATER
  - $X_A$ FOR t5-t8
- RATE OF PARTICULATE
  - $Y_A$ FOR t5-t6
  - 0 FOR t7-t8
- PITCH
  - $Z_A$ FOR t5-t8
- TEMPERATURE
  - DECREASE FROM 50° TO 30° FROM t5-t8

CRUSING STAGE
- WIND SPEED
  - 400 KNOTS FROM t9-t12
- FLOW RATE OF WATER
  - 0 FOR t9-t12
- RATE OF PARTICULATE
  - 0 FOR t9-t12
- PITCH
  - $Z_C$ FOR t9-t12
- TEMPERATURE
  - 20° FROM t9-t12

DESCENT STAGE
- WIND SPEED
  - DECREASE FROM 400 TO 150 KNOTS FROM t13-t16
- FLOW RATE OF WATER
  - 0 FOR t13-t16
- RATE OF PARTICULATE
  - 0 FOR t13-t16
- PITCH
  - $Z_D$ FOR t13-t16
- TEMPERATURE
  - INCREASE FROM 20° TO 50° FROM t13-t16

LANDING STAGE
- WIND SPEED
  - DECREASE FROM 150 TO 0 KNOTS FROM t17-t20
- FLOW RATE OF WATER
  - $X_L$ FOR t17-t20
- RATE OF PARTICULATE
  - $Y_L$ FOR t17-t20
- PITCH
  - $Z_L$ FOR t17-t20
- TEMPERATURE
  - INCREASE FROM 50° TO 70° FROM t17-t20

300

WIND TUNNEL FOR EROSION TESTING

FIELD

This disclosure relates to the field of test systems, and more particularly, to erosion testing.

BACKGROUND

Rain erosion testing is used to test the effects of rain on different types of materials, such as metals, composites, plastics, glass, ceramics, etc. A typical test system, traditionally know as a whirling arm, has a large circular enclosure, an arm that rotates within the enclosure, and water nozzles placed around the enclosure. A specimen under test is attached to the whirling arm. As the arm rotates, droplets of water are emitted from the water nozzles to simulate a rain environment. The rotation speed of the whirling arm simulates a wind speed, and the droplets from the nozzles simulate rain. After the specimen has been exposed to the rain environment for a time period, operators may examine the specimen to determine the effects. For example, a test system may be used to test how rain at 400 knots erodes a material that is used on a wing of an aircraft.

Present test systems such as this are limited in the types of testing that can be performed, the geometry of specimens that can be tested, the environments that can be simulated, etc. Therefore, improved test systems may be desired.

SUMMARY

Embodiments described herein provide improved test systems for simulating an erosion environment. The test systems may be used to test different specimens, such as objects or materials used on an aircraft. For example, an aircraft may be subjected to different conditions during a flight, such as rain, fog, smog, dust, ash, etc. A test system as described herein is able to simulate these conditions to test their effects on a specimen, such as a material on a wing of an aircraft. The test system described herein uses a wind tunnel to simulate wind speed, and injects water droplets and/or other particulates into the air flow of the wind tunnel to simulate rain, sand, dust, etc. The conditions created by the test system can be varied over the duration of the test as desired as can the orientation of the test specimen. Use of a test system as described herein is advantageous because the specimen under test may have virtually any geometry and weight, a wide range of conditions can be simulated, the conditions simulated within the test system can be varied during a test as desired, and the system is safe due to a lack of a very high speed rotating whirling arm.

One embodiment comprises a test system that includes a wind tunnel having a fan unit at a first end and an exhaust unit at an opposing second end, where the fan unit is configured to direct an air flow through the wind tunnel and out of the exhaust unit. The test system includes a test fixture within the wind tunnel that is configured to secure a specimen under test in a path of the air flow, and to adjust an orientation of the specimen relative to the direction of the air flow. The test system includes a water injection unit having a nozzle installed in the wind tunnel between the fan unit and the test fixture that is configured to spray water droplets into the air flow. The test system further includes a controller configured to identify a test profile indicating conditions for a test of the specimen, such as a flight profile for a simulated flight of an aircraft. The controller is configured to vary a speed of the air flow, the orientation of the specimen, and a flow rate of water out of the nozzle of the water injection unit during the test to simulate the conditions indicated in the test profile.

In another embodiment, the controller includes a speed control module configured to control a fan speed of the fan unit to vary the speed of the air flow, and a water control module configured to control water pressure to the nozzle of the water injection unit to vary the flow rate of water out of the nozzle of the water injection unit.

In another embodiment, the controller includes a fixture control module configured to adjust an angle of the test fixture relative to the direction of the air flow to vary the orientation of the specimen.

In another embodiment, the test system further includes a particulate injection unit having a nozzle installed in the wind tunnel between the fan unit and the test fixture that is configured to emit particulates into the air flow, such as sand, dirt, ash, etc. The controller is configured to vary a flow of the particulates into the air flow during the test.

In another embodiment, the controller includes a particulate control module configured to control a particulate-to-air ratio in the particulate injection unit to vary the flow of the particulates into the air flow.

In another embodiment, a catch unit is installed between the test fixture and the exhaust unit. The catch unit includes a nozzle configured to spray a stream of water perpendicularly through the air flow to remove the particulates before exiting out of the exhaust unit, a tank configured to catch the stream of water from the nozzle of the catch unit, and a drain configured to release the water from the tank.

In another embodiment, the controller includes a catch unit control module configured to control a flow rate of the water stream from the nozzle in the catch unit, and a drain control module configured to control the drain to release the water from the tank.

In another embodiment, a filter is installed between the test fixture and the exhaust unit, and is configured to remove the particulates from the air flow before exiting out of the exhaust unit.

In another embodiment, the test system includes a heating and cooling system configured to adjust a temperature in the wind tunnel. The controller includes a temperature control module configured to control the heating and cooling system to adjust the temperature in the wind tunnel to a target temperature.

In another embodiment, the test system includes a camera unit configured to capture video and images of the specimen under test. The controller includes a camera control module configured to turn the camera on and off.

Another embodiment comprises a test system that includes a wind tunnel having a fan unit configured to direct an air flow through the wind tunnel. The test system includes a test fixture within the wind tunnel that is configured to secure a specimen under test in a path of the air flow, and to adjust an orientation of the specimen relative to a direction of the air flow. The test system further includes a water injection unit having a nozzle installed in the wind tunnel between the fan unit and the test fixture that is configured to spray water droplets into the air flow. The test system further includes a controller configured to identify a test profile indicating conditions for a test of the specimen, and to vary the orientation of the specimen during the test to simulate the conditions indicated in the test profile.

The features, functions, and advantages that have been discussed can be achieved independently in various embodiments or may be combined in yet other embodiments, further details of which can be seen with reference to the following description and drawings.

DESCRIPTION OF THE DRAWINGS

Some embodiments of the present invention are now described, by way of example only, with reference to the accompanying drawings. The same reference number represents the same element or the same type of element on all drawings.

FIG. 3 illustrates a flight profile in an exemplary embodiment.

DESCRIPTION

The figures and the following description illustrate specific exemplary embodiments. It will be appreciated that those skilled in the art will be able to devise various arrangements that, although not explicitly described or shown herein, embody the principles described herein and are included within the contemplated scope of the claims that follow this description. Furthermore, any examples described herein are intended to aid in understanding the principles of the disclosure, and are to be construed as being without limitation. As a result, this disclosure is not limited to the specific embodiments or examples described below, but by the claims and their equivalents.

Figure 1:
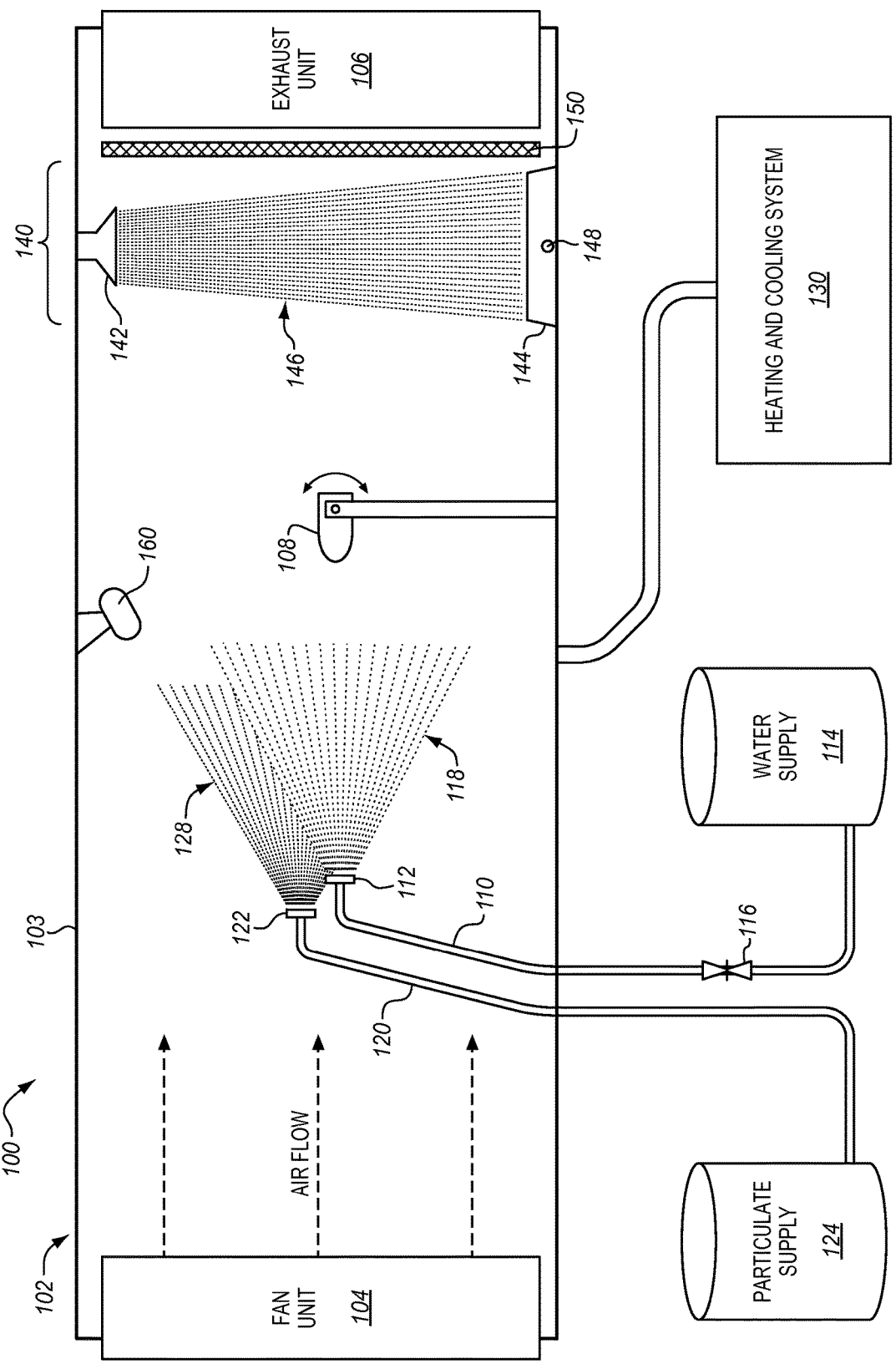
FIG. 1 illustrates a test system for erosion testing in an exemplary embodiment.

FIG. 1 illustrates a test system 100 for erosion testing in an exemplary embodiment. Test system 100 is configured to simulate different environments for testing a specimen. For example, test system 100 may be used to test paints, coatings, plastics, metals, composites, etc. The specimen may be part of an aircraft, where it may be desirable to test the effects of erosion on the specimen during a simulated flight. Test system 100 is able to modify different operating parameters so that the environment can be adjusted as desired during testing.

Test system 100 uses a wind tunnel 102 to simulate wind speed. Wind tunnel 102 includes an enclosure 103 or chamber within which air is moved past a specimen under test. Enclosure 103 may be tubular or may have any desired dimensions. A fan unit 104 is installed at one end of wind tunnel 102, and an exhaust unit 106 is installed at the other end of wind tunnel 102. Fan unit 104 comprises any system that creates a flow of air that moves through wind tunnel 102. Fan unit 104 may include one or more fans or blades that rotate to create the flow of air. Exhaust unit 106 includes one or more openings or vents that expel the air flow out of wind tunnel 102.

Test system 100 also includes a test fixture 108 that is installed in wind tunnel 102 between fan unit 104 and exhaust unit 106. Test fixture 108 comprises any device, fitting, holder, etc., that is able to secure or hold a specimen under test. For example, the specimen under test may be bolted, fastened, clamped, or otherwise affixed to test fixture 108 during testing. Test fixture 108 is adjustable so that the orientation of the specimen under test can likewise be adjusted during a test in relation to the direction of the air flow. Test fixture 108 may include one or more servo motors (not shown) that are able to tilt or rotate test fixture 108 on one, two, or three axes. Therefore, the specimen under test may be oriented in any desired way during testing.

Test system 100 also includes a water injection unit 110 installed in wind tunnel 102 between fan unit 104 and test fixture 108. Water injection unit 110 includes one or more nozzles 112 that are configured to spray water droplets 118 into the air flow. Nozzle 112 receives a flow of water from water supply 114. The flow of water from water supply 114 to nozzle 112 may be controlled by a valve 116 or other flow control mechanism. Valve 116 is able to adjust the water pressure to nozzle 112, which regulates the flow rate through nozzle 112 and also the size of the droplets that are emitted from nozzle 112.

Test system 100 may also include a particulate injection unit 120 installed in wind tunnel 102 between fan unit 104 and test fixture 108. Particulate injection unit 120 includes one or more nozzles 122 that are configured to emit particulates 128 into the air flow. Particulates 128 are particles that simulate an abrasive in air, such as dirt, sand, ash, etc. As pressurized air is forced through particulate injection unit 120, particulate is drawn out of particulate supply 124 and emitted from nozzle 122. The amount of particulate emitted from nozzle 122 is adjustable to a target particulate-to-air ratio. The particulate injection unit 120 is shown in FIG. 1 as being upstream (in the air flow) relative to the water injection unit 110, but the particulate injection unit 120 may be downstream relative to the water injection unit 110 in other embodiments.

Test system 100 may also include a heating and cooling system 130 that is configured to control the temperature inside wind tunnel 102.

Test system 100 may also include a catch unit 140 installed between test fixture 108 and exhaust unit 106. Catch unit 140 is configured to remove particulate that is introduced into the air flow within wind tunnel 102 before the air flow exits through exhaust unit 106. In one embodiment, catch unit 140 includes a nozzle 142 installed toward the top of wind tunnel 102, and a catch tank 144 installed opposite of nozzle 142 toward the bottom of wind tunnel 102. Nozzle 142 is configured to spray water from the top of wind tunnel 102 down perpendicularly through the air flow and into catch tank 144. The spray pattern may be cone-shaped, flat, or any desired pattern. The spray 146 from nozzle 142 filters the particulates from the air (or combined air/water) flow. A drain 148 is installed in catch tank 144 to remove the water and particulate that has accumulated in catch tank 144. Test system 100 may also include a filter 150 installed between test fixture 108 and exhaust unit 106 to further remove particulate from the air flow.

Test system 100 may also include a camera unit 160 installed in wind tunnel 102. Camera unit 160 is aimed at the specimen under test, and is configured to capture images or video of the specimen during a test. Test system 100 may include other features to create the desired erosion environment which are not shown for the sake of brevity.

Figure 2:
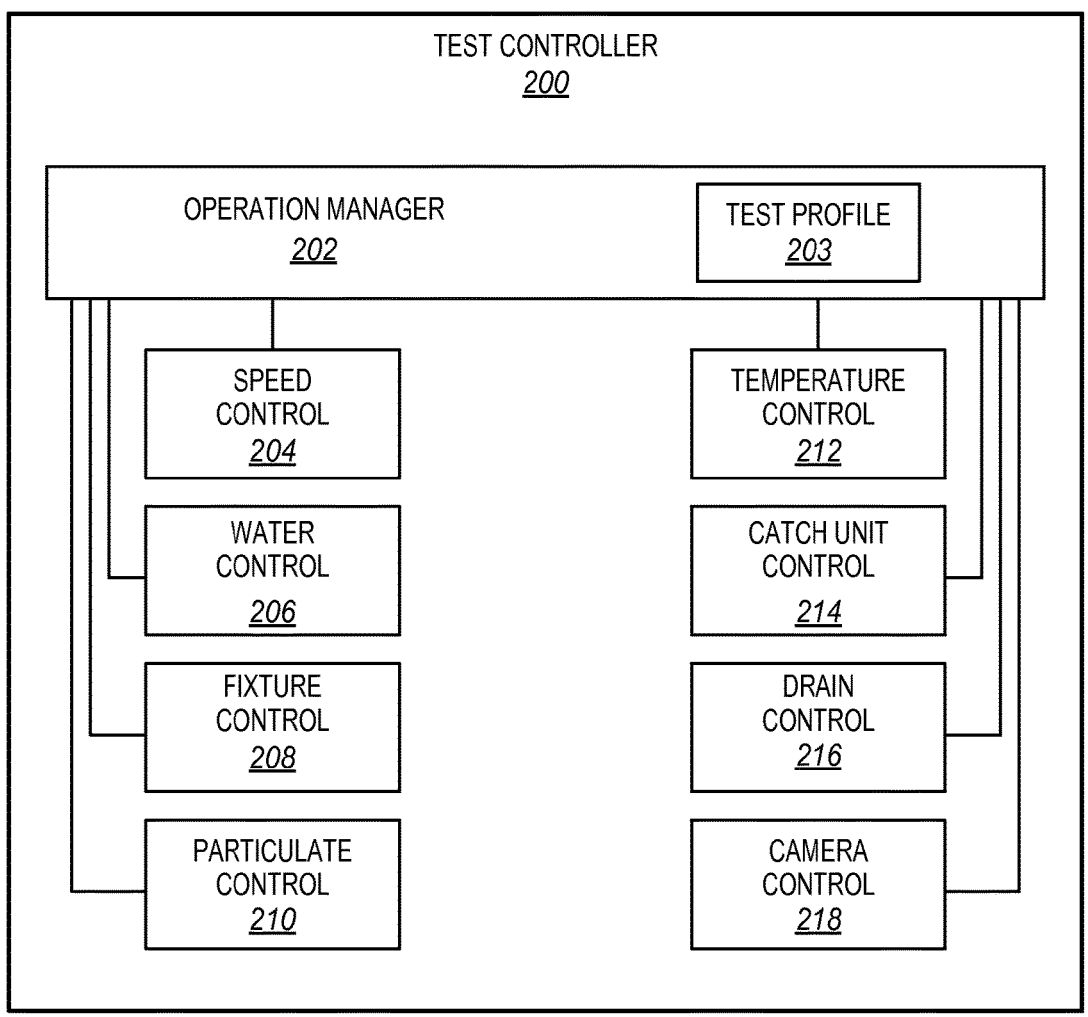
FIG. 2 is a schematic diagram of a test controller in an exemplary embodiment.

FIG. 2 is a schematic diagram of a test controller 200 in an exemplary embodiment. Test controller 200 is a control system that controls the overall operation of test system 100 for performing tests. Test controller 200 may also monitor the overall health of test system 100 in terms of maintaining the specified parameters and shutting the system down if a problem is detected. Test controller 200 includes an operation manager 202 that controls different elements of test system 100 based on one or more test profiles 203. For instance, an operator may program or load test profile 203 onto test controller 200. Test profile 203 indicates conditions for a test run, and comprises a set of actions to perform to simulate the conditions for the test run. Test profile 203 may also indicate parameters for the actions to simulate the conditions for the test run. As one example, test profile 203 may comprise a flight profile for an aircraft to simulate conditions that an aircraft may encounter during flight. A flight profile may include actions and parameters for takeoff, ascent, cruising, descent, and landing. Because environmental conditions may vary during these stages of flight, test profile 203 may vary the actions and parameters to more closely simulate actual flight conditions.

To vary parameters during a test run based on the test profile 203, test controller 200 may include a speed control module 204 that is configured to control a fan speed of fan unit 104. The fan speed of fan unit 104 in turn regulates the rate of the air flow through wind tunnel 102. Test controller 200 may include a water control module 206 that is configured to control water injection unit 110 to adjust a flow rate and/or droplet size out of nozzle 112, or shut off the flow of water to nozzle 112. Water control module 206 may control valve 116 to regulate the flow rate of water from water source 114 to nozzle 112, or may shut valve 116 to shut off the water supply to nozzle 112.

Test controller 200 may include a fixture control module 208 that is configured to control an orientation of test fixture 108 within wind tunnel 102. Fixture control module 208 may provide control signals to test fixture 108 to twist or rotate along one or more axes so that the specimen under test has a desired orientation.

Test controller 200 may include a particulate control module 210 configured to control particulate injection unit 120 to adjust a flow of particulates to nozzle 122, or shut the flow off to nozzle 122. For example, particulate control module 210 may control the air pressure within particulate injection unit 120, the amount of particulate (e.g., through a valve) that is drawn into the pressured air of particulate injection unit 120, or may shut off the supply of particulate in particulate injection unit 120.

Test controller 200 may include a temperature control module 212 configured to control heating and cooling system 130 to adjust the temperature within wind tunnel 102 to a target temperature. For example, temperature control module 212 may instruct system 130 to cool the temperature within wind tunnel 102 below the ambient temperature, or may instruct system 130 to warm the temperature within wind tunnel 102 above the ambient temperature.

Test controller 200 may include a catch unit control module 214 that is configured to control catch unit 140. Catch unit control module 214 may turn catch unit 140 on and off, and may control a flow rate of the water out of nozzle 142 and/or a spray pattern when catch unit 140 is turned on. Test controller 200 may include a drain control module 216 that is configured to control drain 148 to release water that has accumulated in catch tank 144.

Test controller 200 may include a camera control module 218 configured to turn camera 160 on and off. Test controller 200 may include other modules for adjusting the operating parameters of test system 100.

Test system 100 is controllable so that a wide variety of conditions may be simulated during a test run, and different conditions or parameters may be varied during the test run.

The following describes an exemplary process for an erosion test in test system 100. For this example, test controller 200 has loaded a flight profile for an aircraft. FIG. 3 illustrates a flight profile 300 in an exemplary embodiment. Flight profile 300 indicates a takeoff stage, an ascent stage, a cruising stage, a descent stage, and a landing stage for a test flight. The parameters in the flight profile may vary between the different stages, or during a stage. For example, the takeoff stage is for times t1 to t4, and includes parameters for wind speed, flow rate of water, particulate rate, pitch, temperature, etc. For example, the wind speed parameter indicates an increase from zero to 150 knots during time t1 to t4. The flow rate of water parameter has a value of "$X_T$" for time period t1 to t4, the particulate rate has a value of "$Y_T$" for time period t1 to t4, and the pitch parameter has a value of "$Z_T$" for time period t1 to t4. The temperature parameter decreases from 70° F. to 50° F.

The other stages of flight profile 300 include similar parameters. An operator can program different flight profiles to simulate different conditions within test system 100.

Figure 4:
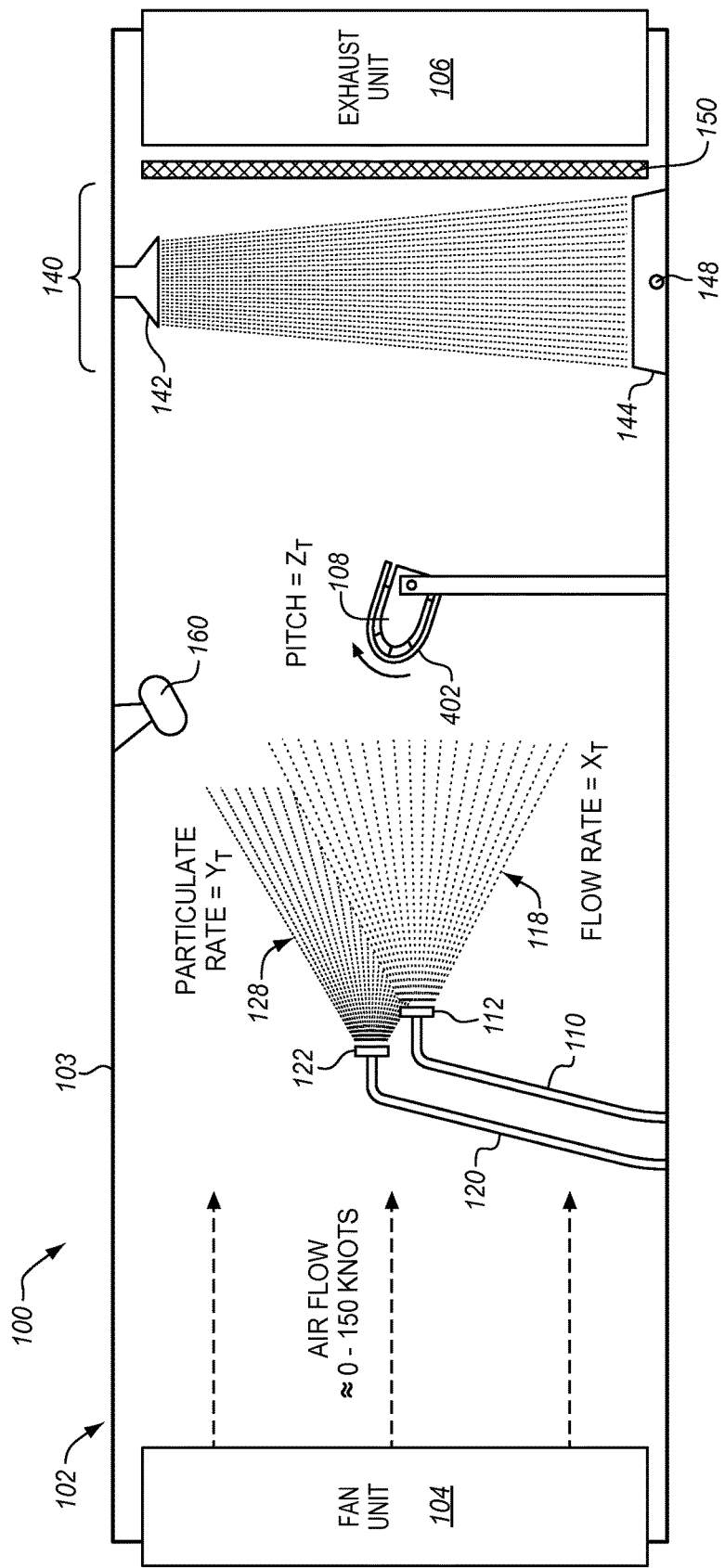
FIG. 4 illustrates the test system simulating a takeoff stage of the flight profile in an exemplary embodiment.

FIG. 4 illustrates test system 100 simulating the takeoff stage of flight profile 300 in an exemplary embodiment. A specimen under test (SUT) 402 is attached to test fixture 108, and it is assumed that SUT 402 is an object or material on an aircraft. The takeoff stage simulates conditions experienced by SUT 402 during takeoff. According to flight profile 300, the parameter for wind speed increases from about 0 knots to 150 knots to simulate the airspeed of an aircraft during takeoff. The parameter for the flow rate of water (out of water injection unit 110) is "$X_T$" to simulate rain during takeoff. The parameter for the particulate rate (out of particulate injection unit 120) is "$Y_T$" to simulate an abrasive in the air during takeoff, such as sand or dirt. The parameter for the pitch of SUT 402 is "$Z_T$" to simulate the pitch of the aircraft during takeoff. Test controller 200 controls test system 100 according to the parameters of flight profile 300. These parameters for the takeoff stage may vary during the duration of the stage.

Figure 5:
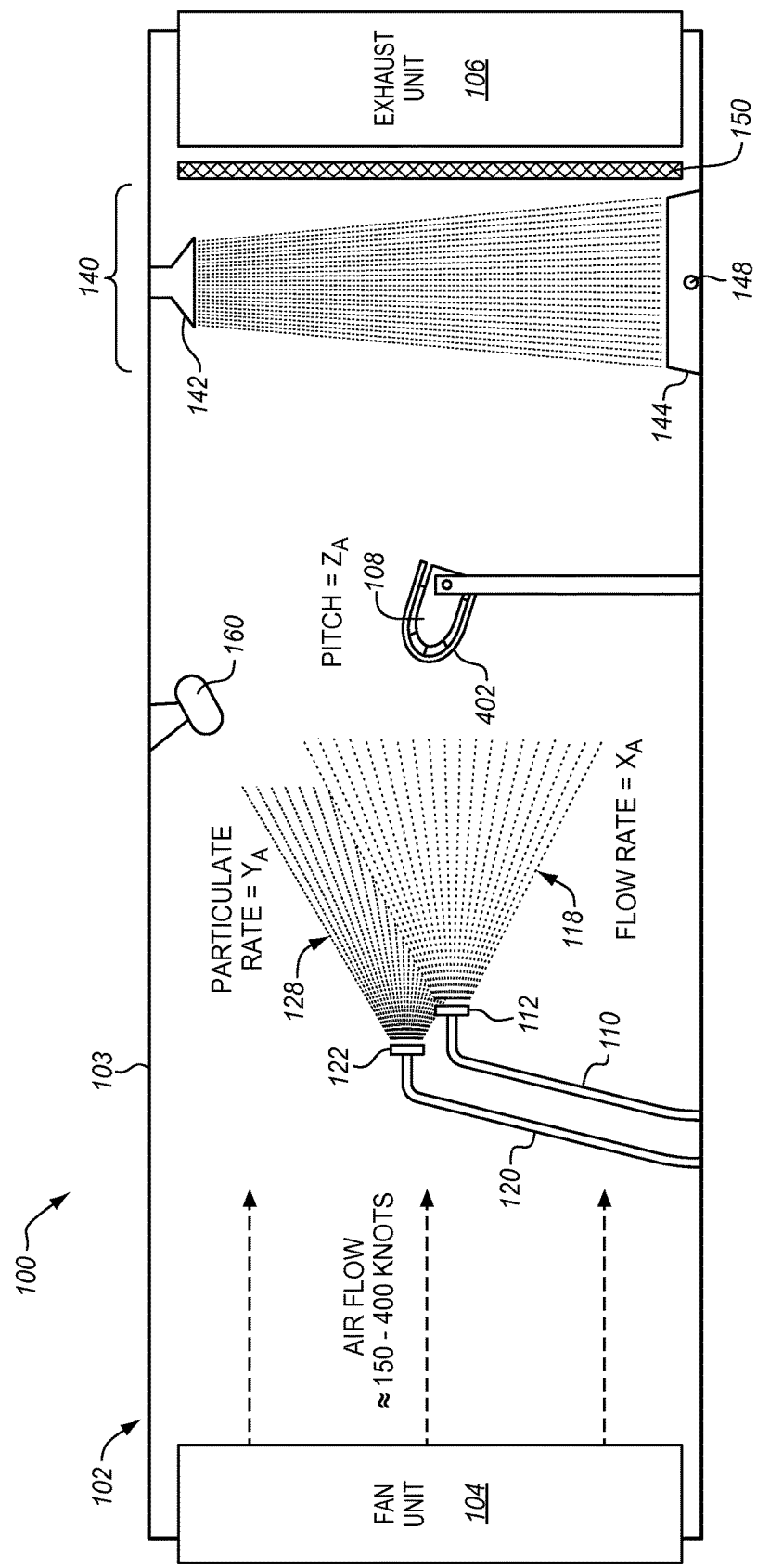
FIGS. 5-6 illustrate the test system simulating an ascent stage of the flight profile in an exemplary embodiment.
Figure 6:
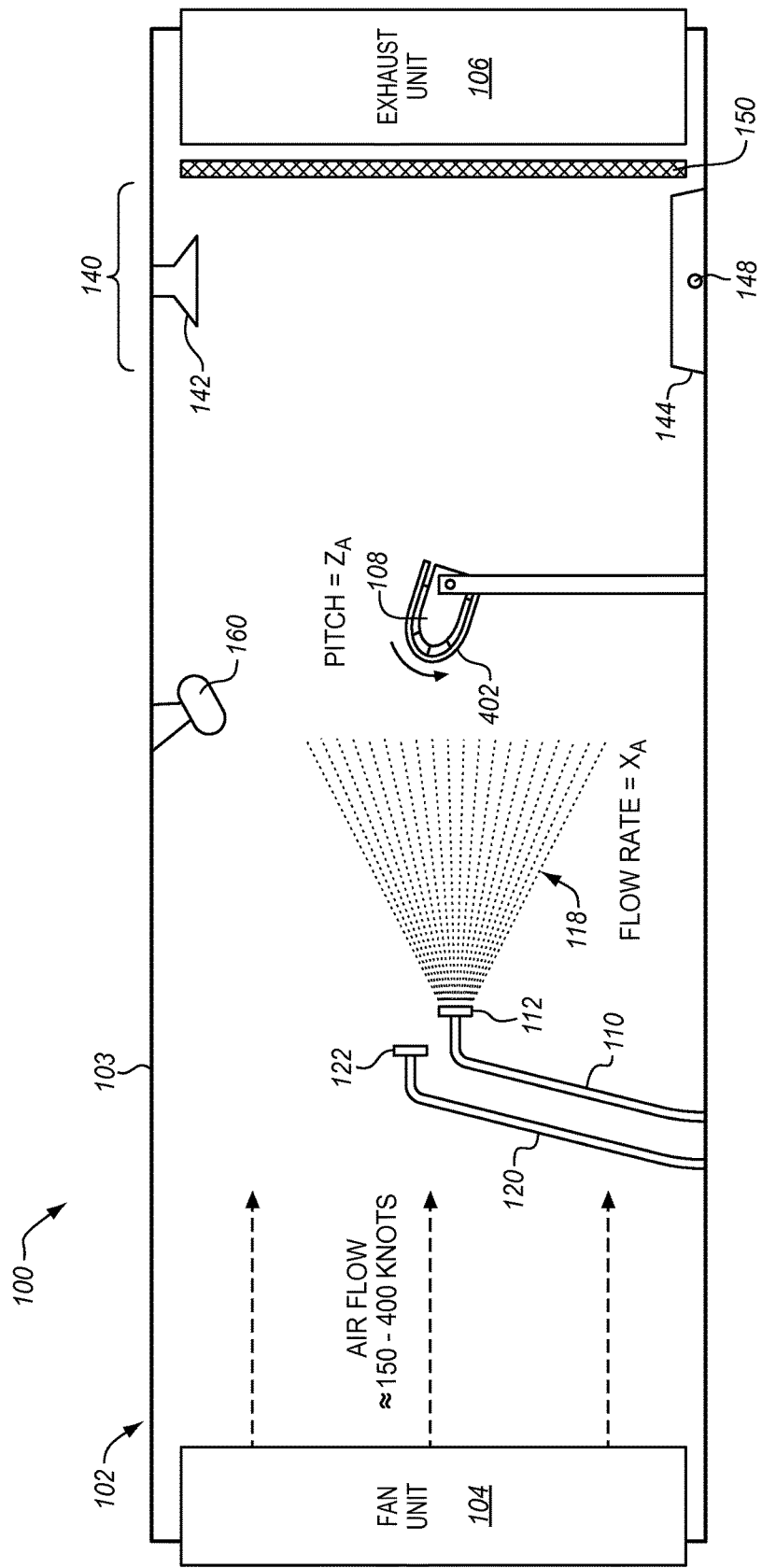

After the takeoff stage, flight profile 300 sequences to the ascent stage. FIGS. 5-6 illustrate test system 100 simulating the ascent stage of flight profile 300 in an exemplary embodiment. The ascent stage simulates conditions experienced by SUT 402 after takeoff while the aircraft ascends to a cruising altitude. According to flight profile 300, the parameter for wind speed increases from about 150 knots to 400 knots to simulate the airspeed of the aircraft (see FIG. 5). The parameter for the flow rate of water is "$X_A$" to simulate rain during ascent. The parameter for the particulate rate is "$Y_A$" to simulate an abrasive in the air. The parameter for the pitch of SUT 402 is "$Z_A$" to simulate the pitch of the aircraft during ascent. These parameters may be different than the parameters in the takeoff stage.

During the ascent stage, the parameter for the particulate rate changes to zero (at time t7-t8) to simulate the aircraft ascending out of dust or dirt in the air (see FIG. 6). Therefore, particulate injection unit 120 no longer emits particulate into the air flow. Because the particulate is no longer being injected into the air flow, test controller 200 deactivates catch unit 140. Test controller 200 may also adjust the pitch of SUT 402 downward during this stage, adjust temperature, etc.

Figure 7:
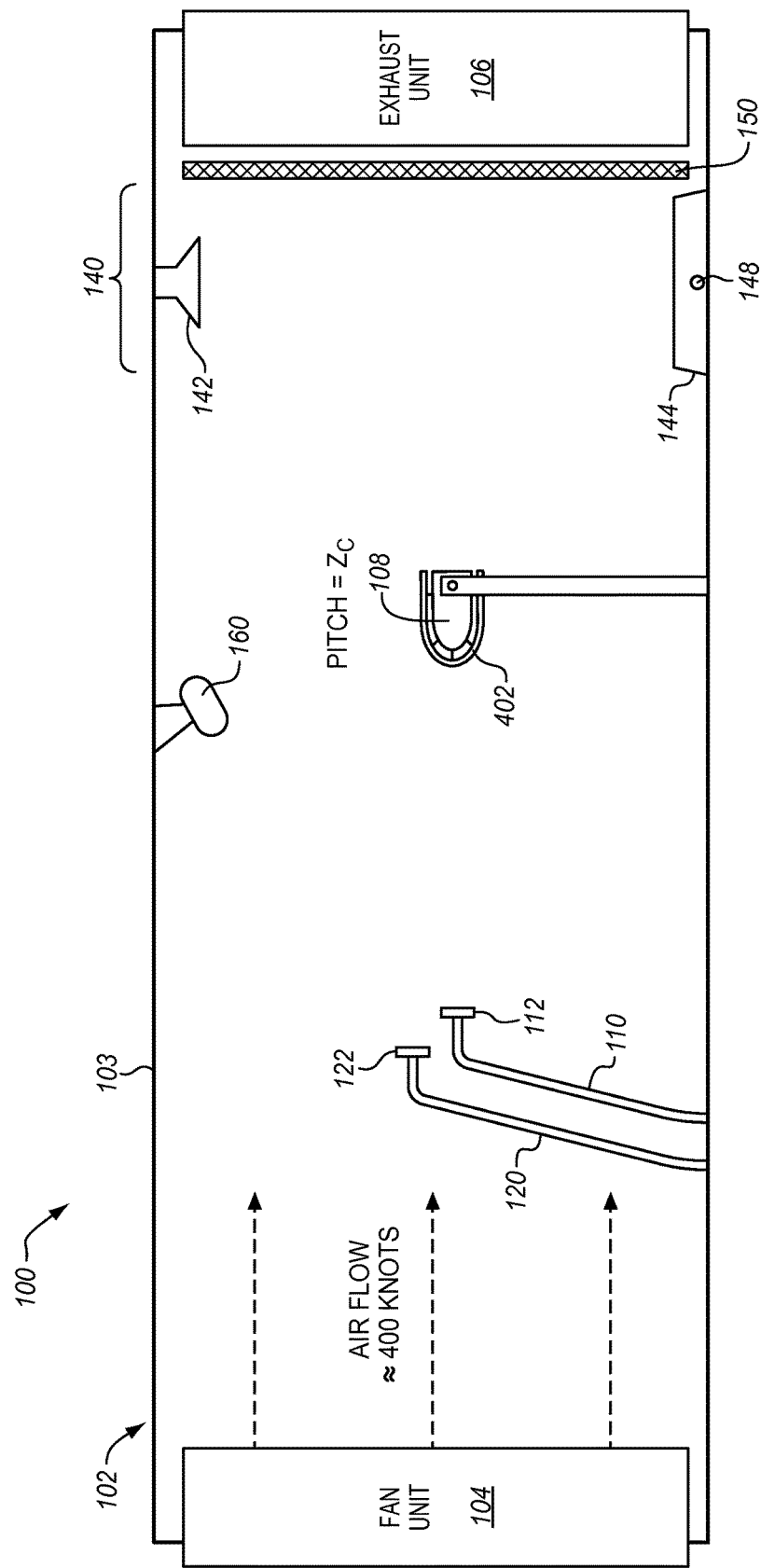
FIG. 7 illustrates the test system simulating a cruising stage of the flight profile in an exemplary embodiment.

After the ascent stage, flight profile 300 sequences to the cruising stage. FIG. 7 illustrates test system 100 simulating the cruising stage of flight profile 300 in an exemplary embodiment. The cruising stage simulates conditions experienced by SUT 402 while the aircraft is at a cruising altitude. According to flight profile 300, the parameter for wind speed is about 400 knots to simulate the airspeed of the aircraft. The parameter for the flow rate of water is zero to simulate the aircraft cruising at an altitude above the rain. The parameter for the particulate rate is also zero. The parameter for the pitch of SUT 402 is "$Z_C$" to simulate the pitch of the aircraft at cruising altitude.

Figure 8:
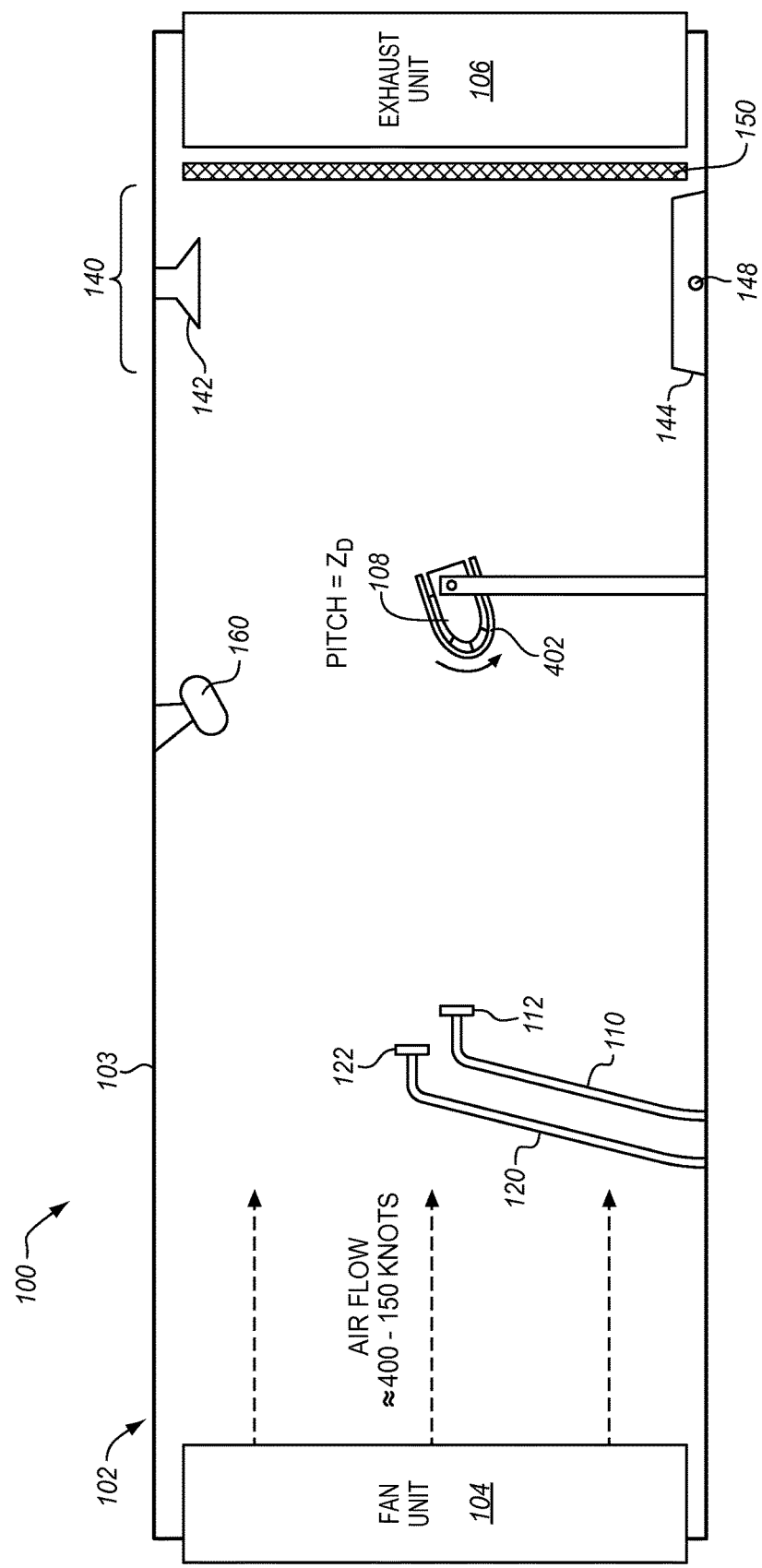
FIGS. 8-9 illustrate the test system simulating a descent stage of the flight profile in an exemplary embodiment.
Figure 9:
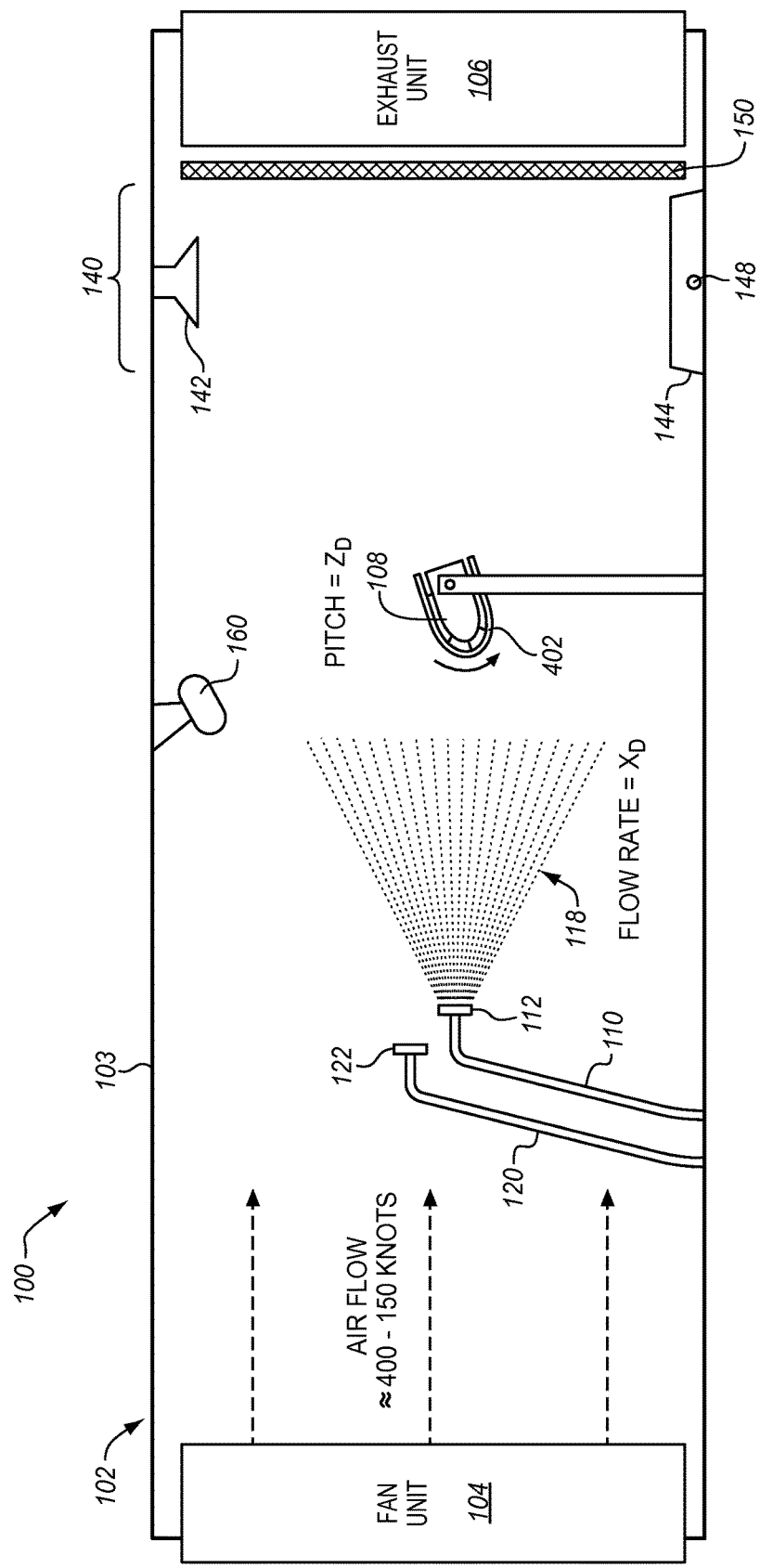

After the cruising stage, flight profile 300 sequences to the descent stage. FIGS. 8-9 illustrate test system 100 simulating the descent stage of flight profile 300 in an exemplary embodiment. The descent stage simulates conditions experienced by SUT 402 during descent of the aircraft. The parameter for wind speed decreases from about 400 knots to 150 knots to simulate the airspeed of the aircraft (see FIG. 8). The parameter for the flow rate of water and the parameter for the particulate rate are still zero. The parameter for the pitch of SUT 402 is "$Z_D$" to simulate the pitch of the aircraft during descent. During the descent stage, the parameter for flow rate of water changes from zero to "$X_D$" to simulate rain during descent (see FIG. 9).

Figure 10:
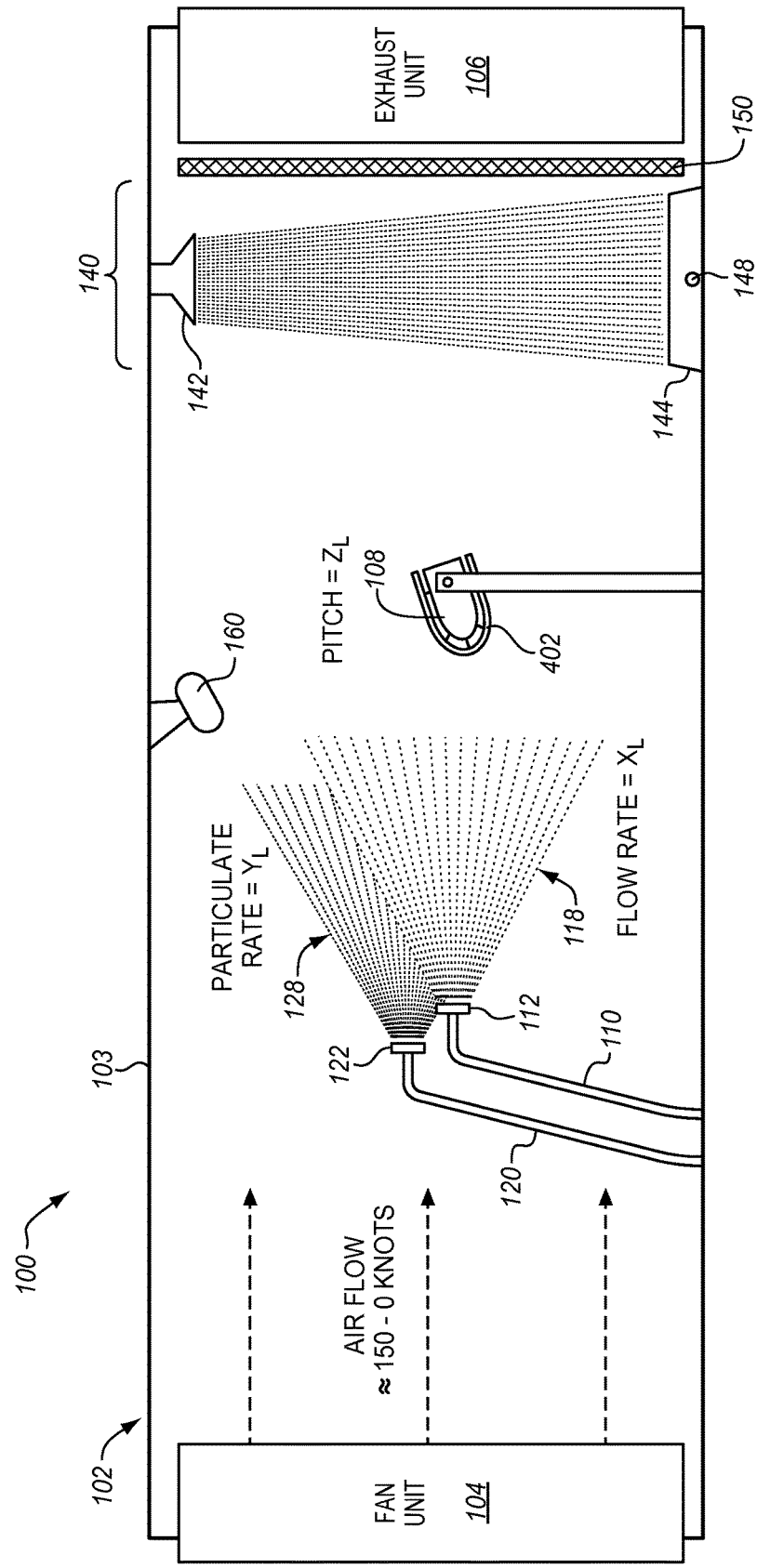
FIG. 10 illustrates the test system simulating a landing stage of the flight profile in an exemplary embodiment.

After the descent stage, flight profile 300 sequences to the landing stage. FIG. 10 illustrates test system 100 simulating the landing stage of flight profile 300 in an exemplary embodiment. The landing stage simulates conditions experienced by SUT 402 during landing of the aircraft. The parameter for wind speed decreases from about 150 knots to 0 knots to simulate the airspeed of the aircraft. The parameter for the flow rate of water is "$X_L$" to simulate rain during landing. The parameter for the particulate rate is "$Y_L$" to simulate an abrasive in the air during landing. The parameter for the pitch of SUT 402 is "$Z_L$" to simulate the pitch of the aircraft during landing. Because particulate is being introduced into the air flow, test controller 200 also activates catch unit 140.

After this test run, SUT 402 may be removed from test system 100 and evaluated to determine the erosion effects of the rain and particulate on SUT 402 during a simulated flight. Test system 100 as described above provides advantages over prior test systems in that a specimen of virtually any geometry and weight can be tested. The wind speed within wind tunnel 102 can be varied, wind tunnel 102 can be heated and cooled, and water and/or particulate can be injected into the air flow, which allows for simulation of a wide range of conditions. The angle, position, inclination, etc., of test fixture 108 may be adjusted so that the orientation of SUT 402 may be adjusted during a test run. Also, test system 100 is programmable and computer-controlled to allow an operator to program a complete profile, such as a profile that allows for accurate simulation of an aircraft from takeoff to landing. Additionally, multiple cycles could be programmed allowing evaluation over multiple flight cycles without a need for a person to actively monitor the system. The control system would be capable of monitoring the key system parameters and shutting the unit down should a problem be detected.

Any of the various elements shown in the figures or described herein may be implemented as hardware, software, firmware, or some combination of these. For example, an element may be implemented as dedicated hardware. Dedicated hardware elements may be referred to as "processors", "controllers", or some similar terminology. When provided by a processor, the functions may be provided by a single dedicated processor, by a single shared processor, or by a plurality of individual processors, some of which may be shared. Moreover, explicit use of the term "processor" or "controller" should not be construed to refer exclusively to hardware capable of executing software, and may implicitly include, without limitation, digital signal processor (DSP) hardware, a network processor, application specific integrated circuit (ASIC) or other circuitry, field programmable gate array (FPGA), read only memory (ROM) for storing software, random access memory (RAM), non-volatile storage, logic, or some other physical hardware component or module.

Also, an element may be implemented as instructions executable by a processor or a computer to perform the functions of the element. Some examples of instructions are software, program code, and firmware. The instructions are operational when executed by the processor to direct the processor to perform the functions of the element. The instructions may be stored on storage devices that are readable by the processor. Some examples of the storage devices are digital or solid-state memories, magnetic storage media such as a magnetic disks and magnetic tapes, hard drives, or optically readable digital data storage media.

Although specific embodiments were described herein, the scope is not limited to those specific embodiments. Rather, the scope is defined by the following claims and any equivalents thereof.

The invention claimed is:

1. A test system comprising:
   a wind tunnel having a fan unit at a first end and an exhaust unit at an opposing second end, wherein the fan unit is configured to direct an air flow through the wind tunnel and out of the exhaust unit;
   a test fixture within the wind tunnel that is configured to secure a specimen under test in a path of the air flow, and to adjust an orientation of the specimen relative to a direction of the air flow;
   a water injection unit having a first nozzle installed in the wind tunnel between the fan unit and the test fixture that is configured to spray water droplets into the air flow;
   a particulate injection unit having a second nozzle installed in the wind tunnel between the fan unit and the test fixture that is configured to emit particulates into the air flow, wherein the particulates are particles that simulate an abrasive in the air flow;
   a controller configured to identify a test profile indicating conditions for a test of the specimen, and to vary a speed of the air flow, the orientation of the specimen, a flow rate of water out of the first nozzle of the water injection unit, and a flow of the particulates into the air flow during the test to simulate the conditions indicated in the test profile; and
   a catch unit installed between the test fixture and the exhaust unit to remove the particulates before exiting out of the exhaust unit, the catch unit comprising:
   a third nozzle installed toward a top of the wind tunnel, and configured to spray water from the top of the wind tunnel and perpendicularly down through the air flow to filter the particulates from the air flow; and
   a catch tank installed toward a bottom of the wind tunnel opposite the third nozzle, and configured to catch the water from the third nozzle.

2. The test system of claim 1 wherein:
   the controller includes:
   a speed control module configured to control a fan speed of the fan unit to vary the speed of the air flow; and
   a water control module configured to control water pressure to the first nozzle of the water injection unit to vary the flow rate of water out of the first nozzle of the water injection unit.

3. The test system of claim 1 wherein:
the controller includes:
  a fixture control module configured to adjust an angle of the test fixture relative to the direction of the air flow to vary the orientation of the specimen.

4. The test system of claim 1 wherein:
the particulate injection unit is upstream in the airflow to the water injection unit.

5. The test system of claim 1 wherein:
the controller includes:
  a particulate control module configured to control a particulate-to-air ratio in the particulate injection unit to vary the flow of the particulates into the air flow.

6. The test system of claim 1 wherein:
the particulates comprise sand, dirt, or ash.

7. The test system of claim 1 wherein:
the catch unit further comprises:
  a drain configured to remove the water and the particulate that has accumulated in the catch tank.

8. The test system of claim 7 wherein:
the controller includes:
  a catch unit control module configured to turn the catch unit on and off, to control a flow rate of the water from the third nozzle when turned on, and to control a spray pattern from the third nozzle; and
  a drain control module configured to control the drain to release the water and the particulate that has accumulated in the catch tank.

9. The test system of claim 1 further comprising:
a filter installed between the test fixture and the exhaust unit, and configured to remove the particulates from the air flow before exiting out of the exhaust unit.

10. The test system of claim 1 further comprising:
a heating and cooling system configured to adjust a temperature in the wind tunnel;
wherein the controller includes:
  a temperature control module configured to control the heating and cooling system to adjust the temperature within the wind tunnel to a target temperature.

11. The test system of claim 1 further comprising:
a camera unit configured to capture images of the specimen under test;
wherein the controller includes:
  a camera control module configured to turn the camera on and off.

12. The test system of claim 1 wherein:
the test profile comprises a flight profile for a simulated flight of an aircraft.

13. A test system comprising:
a wind tunnel having a fan unit at a first end and an exhaust unit at an opposing second end, wherein the fan unit is configured to direct an air flow through the wind tunnel and out of the exhaust unit;
a test fixture within the wind tunnel that is configured to secure a specimen under test in a path of the air flow, and to adjust an orientation of the specimen relative to a direction of the air flow;
a particulate injection unit having a first nozzle installed in the wind tunnel between the fan unit and the test fixture that is configured to emit particulates into the air flow, wherein the particulates are particles that simulate an abrasive in the air flow;
a catch unit installed between the test fixture and the exhaust unit to remove the particulates before exiting out of the exhaust unit, the catch unit comprising:
  a second nozzle installed toward a top of the wind tunnel, and configured to spray water from the top of the wind tunnel and perpendicularly down through the air flow to filter the particulates from the air flow; and
  a catch tank installed toward a bottom of the wind tunnel opposite the second nozzle, and configured to catch the water from the second nozzle; and
a controller configured to identify a test profile indicating conditions for a test of the specimen;
the controller configured to vary a speed of the air flow, the orientation of the specimen, and a flow of the particulates into the air flow during the test to simulate the conditions indicated in the test profile.

14. The test system of claim 13 wherein:
the particulates comprise sand, dirt, or ash.

15. The test system of claim 13 further comprising:
a water injection unit having a third nozzle installed in the wind tunnel between the fan unit and the test fixture that is configured to spray water droplets into the air flow;
wherein the controller is configured to vary a flow rate of water out of the third nozzle of the water injection unit during the test.

16. The test system of claim 13 wherein:
the catch unit further comprises:
  a drain configured to remove the water and the particulate that has accumulated in the catch tank.

17. The test system of claim 13 wherein:
the test profile comprises a flight profile for a simulated flight of an aircraft.

18. A test system comprising:
a wind tunnel having a fan unit configured to direct an air flow through the wind tunnel and out an exhaust unit;
a test fixture within the wind tunnel that is configured to secure a specimen under test in a path of the air flow, and to adjust an orientation of the specimen relative to a direction of the air flow;
a water injection unit having a first nozzle installed in the wind tunnel between the fan unit and the test fixture that is configured to spray water droplets into the air flow;
a particulate injection unit having a second nozzle installed in the wind tunnel between the fan unit and the test fixture that is configured to emit particulates into the air flow, wherein the particulates are particles that simulate an abrasive in the air flow;
a catch unit installed between the test fixture and the exhaust unit to remove the particulates before exiting out of the exhaust unit, the catch unit comprising:
  a third nozzle installed toward a top of the wind tunnel, and configured to spray water in a coned-shape pattern from the top of the wind tunnel and perpendicularly down through the air flow to filter the particulates from the air flow;
  a catch tank installed toward a bottom of the wind tunnel opposite the third nozzle, and configured to catch the water from the third nozzle; and
  a drain configured to remove the water and the particulate that has accumulated in the catch tank; and
a controller configured to identify a test profile indicating conditions for a test of the specimen, to vary the orientation of the specimen, to vary a flow rate of water out of the first nozzle of the water injection unit, and to vary a flow of the particulates into the air flow during the test to simulate the conditions indicated in the test profile.

19. The test system of claim 18 wherein:
the test profile comprises a flight profile for a simulated flight of an aircraft.

* * * * *